United States Patent
Chen

(10) Patent No.: US 9,924,020 B2
(45) Date of Patent: Mar. 20, 2018

(54) WEARABLE ELECTRONIC DEVICE AND CONTROL METHOD

(71) Applicant: Lenovo (Beijing) Limited, Beijing (CN)

(72) Inventor: Xingwen Chen, Beijing (CN)

(73) Assignee: Lenovo (Beijing) Limited, Beijing (CN)

( * ) Notice: Subject to any disclaimer, the term of this patent is extended or adjusted under 35 U.S.C. 154(b) by 0 days.

(21) Appl. No.: 15/373,321

(22) Filed: Dec. 8, 2016

(65) Prior Publication Data

US 2017/0187861 A1 Jun. 29, 2017

(30) Foreign Application Priority Data

Dec. 23, 2015 (CN) .......................... 2015 1 0980653

(51) Int. Cl.
| | |
|---|---|
| *H04B 7/00* | (2006.01) |
| *H04M 1/725* | (2006.01) |
| *H04B 1/3827* | (2015.01) |
| *A61B 5/00* | (2006.01) |
| *A61B 5/11* | (2006.01) |

(52) U.S. Cl.
CPC .......... *H04M 1/7253* (2013.01); *A61B 5/002* (2013.01); *A61B 5/6807* (2013.01); *A61B 5/6829* (2013.01); *H04B 1/385* (2013.01); *H04B 1/3833* (2013.01); *A61B 5/1123* (2013.01); *A61B 5/7475* (2013.01); *A61B 2503/12* (2013.01); *A61B 2505/09* (2013.01); *A61B 2560/0242* (2013.01); *H04B 2001/3855* (2013.01)

(58) Field of Classification Search
None
See application file for complete search history.

(56) References Cited

U.S. PATENT DOCUMENTS

| | | | | |
|---|---|---|---|---|
| 2010/0030343 A1* | 2/2010 | Hansen | ........... | A61F 2/6607 623/47 |
| 2010/0037489 A1 | 2/2010 | Berner, Jr. et al. | | |
| 2010/0275338 A1* | 11/2010 | Hyde | ........... | A61B 5/1077 2/69 |
| 2015/0157087 A1* | 6/2015 | Blumenthal | ........... | A43B 21/42 36/100 |
| 2015/0182844 A1* | 7/2015 | Jang | ........... | G01G 19/50 700/91 |
| 2016/0204332 A1* | 7/2016 | Hunt | ........... | H01L 41/042 318/16 |
| 2016/0345663 A1* | 12/2016 | Walker | ........... | A43B 13/143 |

FOREIGN PATENT DOCUMENTS

| | | |
|---|---|---|
| CN | 204273392 U | 4/2015 |
| CN | 105029823 A | 11/2015 |
| CN | 105077835 A | 11/2015 |

* cited by examiner

*Primary Examiner* — Mohammed Rachedine
(74) *Attorney, Agent, or Firm* — Ference & Associates LLC

(57) ABSTRACT

Disclosed is a wearable electronic device, including: an adjustment apparatus that adjusts a spatial form of the wearable device; and a control apparatus in communication with the adjustment apparatus, wherein the control apparatus drives, responsive to detection of an adjustment parameter, the adjustment apparatus to perform a spatial form adjustment for the wearable device. Other aspects are described and claimed.

17 Claims, 3 Drawing Sheets

US 9,924,020 B2

WEARABLE ELECTRONIC DEVICE AND CONTROL METHOD

CLAIM FOR PRIORITY

This application claims priority to Chinese Application No. 201510980653.5, filed on Dec. 23, 2015, the contents of which are fully incorporated by reference herein.

TECHNICAL FIELD

The subject matter relates to the technical field of wearable electronic devices, and in particular, to a wearable electronic device and a control method.

BACKGROUND

With the continuous development of science and technology, more and more wearable electronic devices are used in people's daily life and work, thereby enormously facilitating people's daily life and work, and becoming an indispensable and important tool for people today. After a typical wearable electronic device is worn, a form is fixed. Therefore, in one state, a user is comfortable with the wearable electronic device, but in another state, a comfort level is reduced.

BRIEF SUMMARY

In summary, one aspect provides a wearable electronic device, comprising: an adjustment apparatus that adjusts a spatial form of the wearable device; and a control apparatus in communication with the adjustment apparatus, wherein the control apparatus drives, responsive to detection of an adjustment parameter, the adjustment apparatus to perform a spatial form adjustment for the wearable device.

Another aspect provides a method, comprising: detecting, at a wearable device, an adjustment parameter related to a spatial form adjustment for the wearable device; and adjusting, using a control unit of the wearable device, the spatial form of the wearable device based on the adjustment parameter that is detected.

A further aspect provides a computer program product, comprising: a computer readable storage device comprising code, the code being executable by a processor of a wearable device and comprising: code that detects, at a wearable device, an adjustment parameter related to a spatial form adjustment for the wearable device; and code that adjusts, using a control unit of the wearable device, the spatial form of the wearable device based on the adjustment parameter that is detected The foregoing is a summary and thus may contain simplifications, generalizations, and omissions of detail, consequently, those skilled in the art will appreciate that the summary is illustrative only and is not intended to be in any way limiting.

For a better understanding of embodiments, together with other and further features and advantages thereof, reference is made to the following description, taken in conjunction with the accompanying drawings, and the scope of the invention will be pointed out in the appended claims.

DETAILED DESCRIPTION

Figure 1:
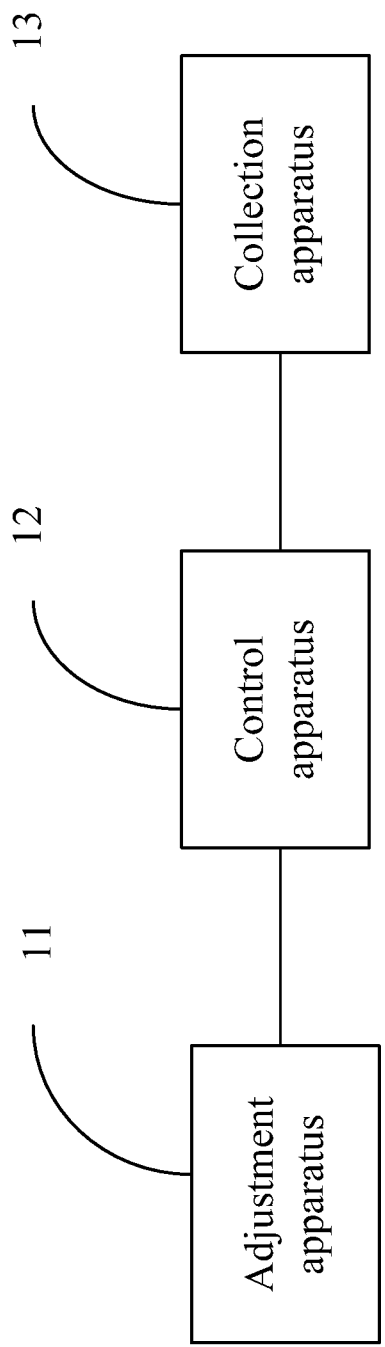
FIG. 1 is a schematic structural diagram of an example electronic device according to an embodiment.
Figure 2:
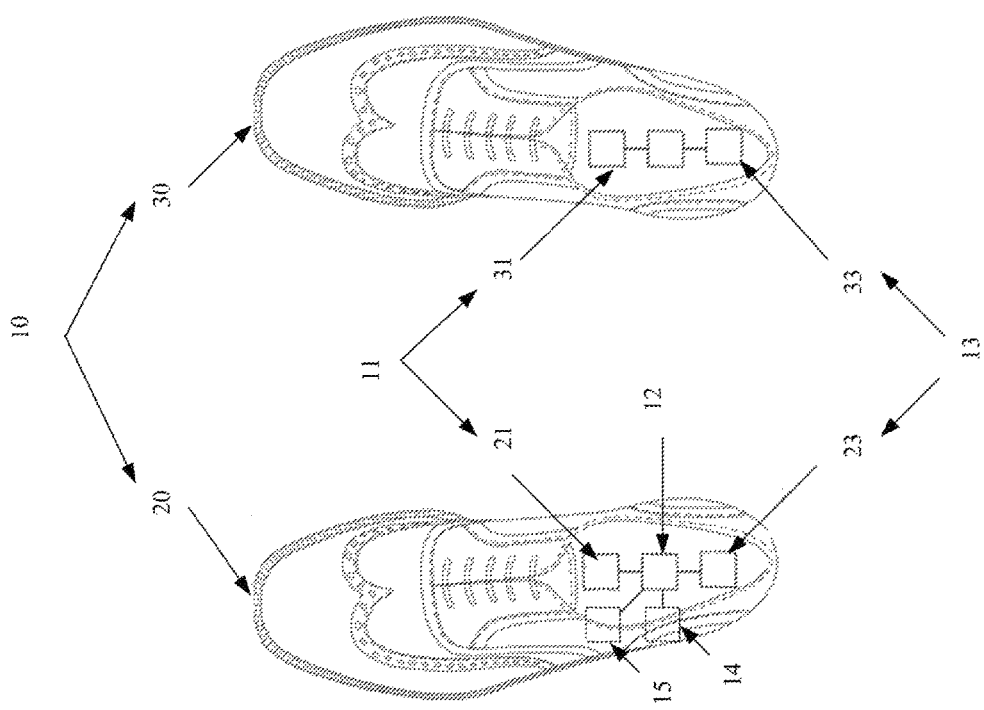
FIG. 2 is a schematic structural diagram of an example wearable electronic device according to an embodiment.
Figure 3:
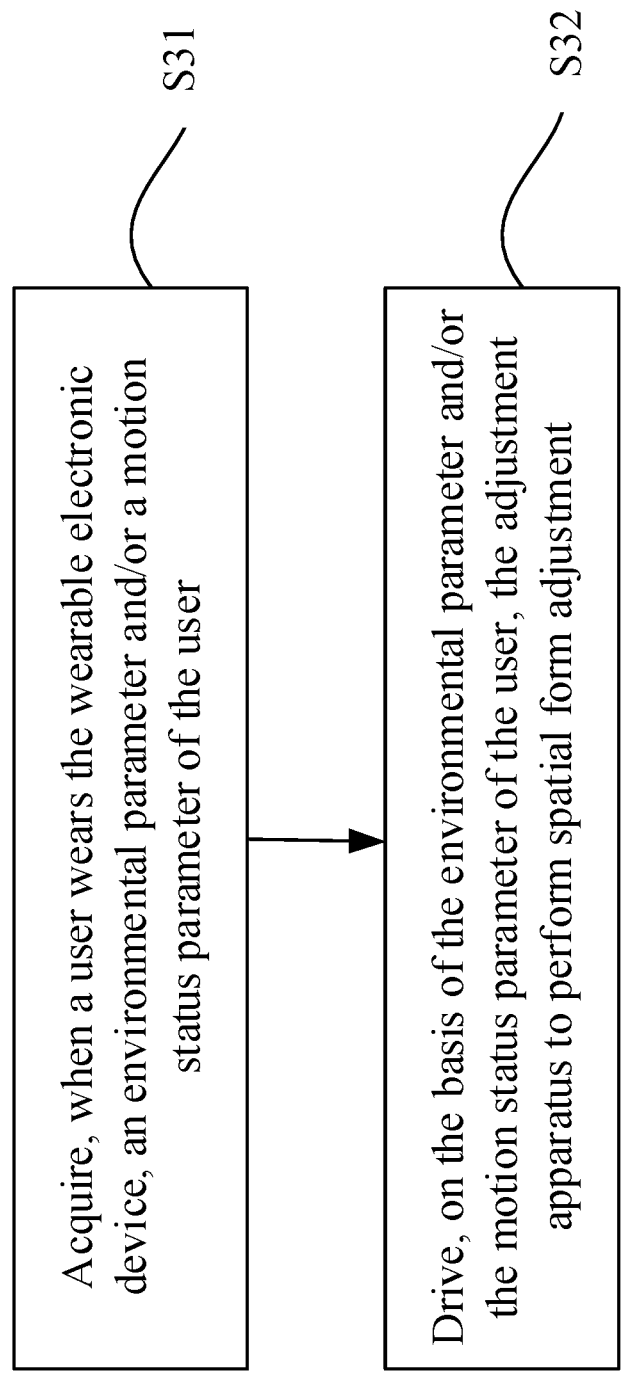
FIG. 3 is a schematic flow diagram of an example method according to an embodiment.

It will be readily understood that the components of the embodiments, as generally described and illustrated in the figures herein, may be arranged and designed in a wide variety of different configurations. Thus, the following more detailed description of the embodiments of the apparatus and method, as represented in FIGS. 1 through 3 is not intended to limit the scope of the embodiments, as claimed, but is merely representative of selected embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, to provide a thorough understanding of embodiments. One skilled in the relevant art will recognize, however, that the embodiments may be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

After a typical wearable electronic device is worn, a form is fixed. Therefore, in one state, a user is comfortable with the wearable electronic device, but in another state, a comfort level is reduced. Using smart shoes as an example, a user needs different comfort levels according to different road surface conditions and different wearing environments.

Based on the foregoing problem, embodiments provide a wearable electronic device. An example structure of a wearable electronic device is shown in FIG. 1.

In this non-limiting example, a wearable electronic device comprises: a retaining apparatus, wherein the retaining apparatus may be configured to retain, when the wearable electronic device is worn by a user, a relative positional relationship between the wearable electronic device and the user; an adjustment apparatus 11, wherein the adjustment apparatus 11 may be configured to adjust a spatial form of the retaining apparatus; a collection apparatus 13, wherein the collection apparatus 13 may be configured to collect an environmental parameter and/or a motion status parameter of the user; and a control apparatus 12, wherein the control apparatus 12 may be configured to drive, on the basis of the environmental parameter and/or the motion status parameter, the adjustment apparatus to perform a spatial form adjustment, so as to adjust the spatial form of the retaining apparatus.

The retaining apparatus is not shown in FIG. 1. The adjustment apparatus 11, the control apparatus 12, and the collection apparatus 13 may be disposed on the retaining apparatus. The adjustment apparatus 11 and the collection apparatus 13 may be separately connected to the control apparatus 12.

When the wearable electronic device is a watch, the retaining apparatus may be a watch band. The positioning apparatus may be a wristband body. When the retaining apparatus is a shoe, the retaining apparatus may be a shoe body. In this non-limiting example, a spatial form may include, but is not limited to, a degree of ventilation, a degree of tightness, and height.

The wearable electronic device may adjust the spatial form according to an environmental parameter and/or a motion status parameter of the user, and may further adjust a comfort level of the user when the user wears the wearable electronic device, so as to enable the user to have relatively good comfort levels when in different states of motion and different wearing environments.

A wearable electronic device may be a pair of smart running shoes, and in this case, an example structure of the wearable electronic device is shown in FIG. 2.

Referring to FIG. 2, shown is a schematic structural diagram of a wearable electronic device according to an embodiment. The wearable electronic device comprises: a retaining apparatus 10, wherein the retaining apparatus 10 is configured to retain, when the wearable electronic device is worn by a user, a relative positional relationship between the wearable electronic device and the user; an adjustment apparatus 11, wherein the adjustment apparatus 11 is configured to adjust a spatial form of the retaining apparatus; a collection apparatus 13, wherein the collection apparatus 13 is configured to collect an environmental parameter and/or a motion status parameter of the user; and a control apparatus 12, wherein the control apparatus 12 is configured to drive, on the basis of the environmental parameter and/or the motion status parameter, the adjustment apparatus to perform a spatial form adjustment so as to adjust the spatial form of the retaining apparatus.

The retaining apparatus 10 comprises: a first retaining unit 20 configured to hold at a first part of a body of the user, and a second retaining unit 30 configured to hold at a second part of the body of the user.

An adjustment apparatus 11 comprises: a first adjustment unit 21 disposed at the first retaining unit 20 and a second adjustment unit 31 disposed at the second retaining unit 30. The first adjustment unit 21 is configured to adjust a spatial form of the first retaining unit 20, and the second adjustment unit 30 is configured to adjust a spatial form of the second retaining unit 30.

A collection apparatus 13 comprises a first collection unit 23 disposed on the first retaining unit 20 and a second collection unit 33 disposed on the second retaining unit 30. The first collection unit 23 may be configured to collect an environmental parameter of an environment in which the first part of the body of the user may be located and/or a motion status parameter of the first part. The second collection unit 33 may be configured to collect an environmental parameter of an environment in which the second part of the body of the user is located and/or a motion status parameter of the first part.

In FIG. 2, the control apparatus 12 may be disposed on the first retaining unit 20. The first retaining unit 20 is provided with a first communication unit 14 connected to the control apparatus. The first communication unit 14 is configured to exchange data with the second adjustment unit 31. The control apparatus 12 wirelessly drives the second adjustment unit 31 through the first communication apparatus 14.

The control apparatus 12 may be disposed on the second retaining unit 20. In this case, the first adjustment unit 21 may be wirelessly connected to the control apparatus 12, and the second adjustment unit 31 may be directly connected to the control apparatus 12.

The first communication apparatus 14 may be further configured to exchange data with a mobile terminal. The control apparatus 12 may be further configured to establish a communication connection to the mobile terminal through the first communication apparatus 14. By means of the connection between the control apparatus 12 and the mobile terminal, the control apparatus 12 may further receive a control signal input by the mobile terminal. The control apparatus 12 may drive, according to the control signal, the first adjustment unit 21 to adjust a spatial form of the first retaining unit 20, and may drive the second adjustment unit 31 to adjust a spatial form of the second retaining unit 30 so as to adjust a comfort level. A communication connection of the control apparatus 12 to the second adjustment unit 31 and the mobile terminal may be achieved through the first communication apparatus 14.

The first communication apparatus 14 may be configured to enable the control apparatus 12 to establish a communication connection to the second adjustment unit 31. In this case, to enable the control apparatus 12 to establish a communication connection to a mobile terminal, the wearable electronic device may further comprise: a second communication unit 15 disposed on the retaining apparatus 10 and connected to the control apparatus 12, wherein the second communication unit 15 may be configured to exchange data with the mobile terminal. The control apparatus 12 may be further configured to establish a communication connection to the mobile terminal through the second communication unit 15. The second communication unit 15 may be configured to receive a control signal of the mobile terminal. The control apparatus 12 may be further configured to drive, according to the control signal, the adjustment apparatus 11 to perform a spatial form adjustment.

The control apparatus 12 may establish a near field communication (NFC) connection to the second adjustment unit 31 through the first communication apparatus 14, and may establish a telecommunication connection to the mobile terminal through the second communication unit 15. A communication apparatus for telecommunication may not be required when the control apparatus 12 communicates with the second adjustment unit 31, thereby reducing communication consumption.

The first retaining unit 20 may include a first cavity with an opening. The second retaining unit 30 may include a second cavity with an opening. After the first part of the body of the user enters into the first cavity, a relative position of the first retaining unit and the body of the user may be retained. After the second part of the body of the user enters into the second cavity, a relative position of the second retaining unit and the body of the user may be retained.

The control apparatus 12 may be configured to drive, on the basis of the environmental parameter and/or the motion status parameter, the adjustment apparatus to perform a spatial form adjustment, so as to adjust a spatial form of the retaining apparatus, thereby adjusting a comfort level. Adjustment modes may include, but are not limited to, the following three example modes.

In on mode one, the first adjustment unit 21 comprises: a first ventilation switch mechanism disposed on a cavity wall of the first cavity. The second adjustment unit 31 comprises: a second ventilation switch mechanism disposed on a side wall of the second cavity. The control apparatus is in communication connection with the first ventilation switch mechanism and the second ventilation switch mechanism. The control apparatus drives, according to the environmental parameter and/or the motion status parameter, the first ventilation switch mechanism and the second ventilation switch mechanism to adjust a degree of ventilation so as to adjust the degrees of ventilation in the first cavity and the second cavity.

In mode two, the first adjustment unit 21 comprises: a first spatial locking mechanism disposed on the opening of the first cavity. The second adjustment unit 31 comprises: a second locking mechanism disposed on the opening of the second cavity. The control apparatus is in communication connection with the first locking mechanism and the second locking mechanism. The control apparatus drives, according to the environmental parameter and/or the motion status parameter, the first locking mechanism and the second locking mechanism to adjust a degree of tightness so as to adjust tightness between a cavity wall of the first cavity and the first part, and adjust tightness between a cavity wall of the second cavity and the second part.

In mode three, the first adjustment unit 21 comprises: a first height adjustment mechanism disposed at the bottom of the first cavity. The second adjustment unit 21 comprises: a second height adjustment mechanism disposed at the bottom of the second cavity. The control apparatus is in communication connection with the first height adjustment mechanism and the second height adjustment mechanism. The control apparatus drives, according to the environmental parameter and/or the motion status parameter, the first height adjustment mechanism and the second height adjustment mechanism to adjust a height, so as to adjust the height of a set area at the bottom of the first cavity and the height of a set area at the bottom of the second cavity.

An environmental parameter may be an environmental parameter of a part of the user that is in contact with the retaining apparatus. An environmental parameter may comprise: one or more of a pressure parameter, an altitude parameter, a temperature parameter, and a humidity parameter.

A motion status parameter may be a motion status parameter of a body part of the user that wears the wearable electronic device. A motion status parameter may include: one or more of a speed, duration, and a motion type.

A method for driving, by the control apparatus 12 on the basis of the environmental parameter and/or the motion status parameter, the adjustment apparatus to perform a spatial form adjustment may include determining whether the environmental parameter and/or the motion status parameter are/is within set threshold ranges/a set threshold range; and if not, adjusting the environmental parameter and/or the motion status parameter, so as to enable the environmental parameter and/or the motion status parameter to be within the set threshold ranges/the set threshold range.

An environmental parameter and/or the motion status parameter are/is within the set threshold ranges/the set threshold range in real time, thereby ensuring a relatively good wearing comfort level.

The wearable electronic device may further be a pair of smart glasses, a smart wristband, a smart watch, and the like. The wearable electronic device may adjust a spatial form in real time on the basis of an environmental parameter and/or a motion status parameter, so as to enable a user to have relatively high comfort levels in different states.

A control method may be applied to the wearable electronic device. An example control method is shown in FIG. 3. The control method includes, at Step S31 acquiring, when a user wears the wearable electronic device, an environmental parameter and/or a motion status parameter of the user. At Step S32, on the basis of the environmental parameter and/or the motion status parameter of the user, driving of the adjustment apparatus performs a spatial form adjustment.

The control method further includes acquiring a control signal of a mobile terminal and driving, according to the control signal, the adjustment apparatus to perform a spatial form adjustment.

The control method further includes adjusting a spatial form of a first retaining unit, and adjusting a spatial form of a second retaining unit, where the first retaining unit is configured to retain a first body at a first part of a body of the user, and the second retaining unit is configured to retain a second body at a second part of the body of the user.

By way of example, adjusting a spatial form of a first retaining unit, and the adjusting a spatial form of a second retaining unit, includes adjusting a degree of ventilation in a first cavity, and adjusting a degree of ventilation in a second cavity, wherein the first retaining unit has the first cavity and the second retaining unit has the second cavity. After the first part of the body of the user enters into the first cavity, a relative position of the first retaining unit and the body of the user may be retained. After the second part of the body of the user enters into the second cavity, a relative position of the second retaining unit and the body of the user may be retained.

Adjusting a spatial form of a first retaining unit, and the adjusting a spatial form of a second retaining unit may include adjusting a degree of tightness between a cavity wall of a first cavity and the first part of the body of the user, and adjusting a degree of tightness between a cavity wall of a second cavity and the second part of the body of the user.

Adjusting a spatial form of a first retaining unit, and the adjusting a spatial form of a second retaining unit may include adjusting the height of a set area at the bottom of the first cavity, and adjusting the height of a set area at the bottom of the second cavity. The first retaining unit has the first cavity. The second retaining unit has the second cavity.

According to the various embodiments, a control method may be applied to a wearable electronic device. A control method and the wearable electronic device may supplement each other for the description of identical and similar features; therefore, details will not be repeated herein. The control method may automatically adjust a spatial form of a wearable electronic device so as to enable a user to have relatively high comfort levels in different states.

Those skilled in the art should realize that an embodiment may be provided as a method, a system or a computer program product. Therefore, various embodiments may use forms of a full hardware embodiment, a full software embodiment, or an embodiment that is a combination of software and hardware. Furthermore, the embodiments may use forms of computer program products implemented on one or more computer storage media or devices (including, but not limited, to a magnetic disk memory device, a CD-ROM device, an optical memory device or the like), which include a computer program code.

Various embodiments are described with reference to flow diagrams and/or block diagrams. It should be understood that each flow and/or block in the flow diagrams and/or block diagrams and a combination thereof may be implemented by computer program instructions. These computer program instructions may be provided for a processor or processors of programmable data processing device(s) to generate a machine, so as to generate an apparatus configured to implement designated functions in one or more flows of a flow diagram and/or one or more blocks of a block diagram by instructions, executed by a processor.

These computer program instructions may also be stored in a computer-readable storage device such as a computer or wearable device memory that can guide a computer or other programmable data processing device(s) to work in a particular way, so that the instructions stored in the computer-readable storage device or memory generate a manufactured product including instructions that implement the designated functions in one or more flows of a flow diagram and/or one or more blocks of a block diagram. In the context of this document, a computer-readable memory or storage device is not a signal and "non-transitory" includes all media except signal media.

The computer program instructions may also be loaded on a computer or other programmable data processing devices, to execute a series of operating steps on the computer or other programmable device(s) to produce a computer executed process, so that instructions executed on the computer or other programmable device(s) provide steps that implement designated functions in one or more flows of a flow diagram and/or one or more blocks of a block diagram.

Although example embodiments have been described, those skilled in the art may make additional alterations and modifications on these embodiments. Therefore, the appended claims are intended to be interpreted as covering the example embodiments, including equivalents and all alterations and modifications falling within the ability of those having skill in the art.

It will be apparent to those skilled in the art that various modifications and variations can be made to the example embodiments without departing from the spirit and scope of the disclosure. In view of the foregoing, the non-limiting example embodiments are to be construed as covering modifications and variations thereof

What is claimed is:

1. A wearable electronic device, comprising:
    an adjustment apparatus that adjusts a spatial form of the wearable device; and
    a control apparatus in communication with the adjustment apparatus, wherein the control apparatus automatically drives, responsive to detection of an adjustment parameter and without user control input, the adjustment apparatus to perform a spatial form adjustment for the wearable device, wherein the adjustment parameter is selected from the group consisting of an environmental parameter and a mode indication;
    wherein the adjustment apparatus changes ventilation of the wearable device relative to a body part of the user.

2. The wearable electronic device according to claim 1, further comprising a communication unit, wherein the communication unit exchanges data with a mobile terminal.

3. The wearable electronic device according to claim 2, wherein the adjustment parameter is received by the communication unit from the mobile terminal.

4. The wearable electronic device according to claim 1, further comprising a part that retains a body part of a user.

5. The wearable electronic device according to claim 4, wherein the part defines a cavity with an opening.

6. The wearable electronic device according to claim 5, wherein, after the body part of the user enters the cavity, a relative position of the part and the body part of the user is sensed and retained.

7. The wearable electronic device according to claim 6, wherein:
    the control apparatus detects that the relative position has changed; and
    the control apparatus thereafter drives the adjustment apparatus to adjust the wearable device.

8. The wearable electronic device according to claim 1, wherein the adjustment apparatus changes a relative tightness of the wearable device relative to a body part of the user.

9. A method, comprising:
    detecting, at a wearable device, an adjustment parameter related to a spatial form adjustment for the wearable device, wherein the adjustment parameter is selected from the group consisting of an environmental parameter and a mode indication; and
    automatically adjusting, using a control unit in communication with an adjustment apparatus of the wearable device and without user control input, the spatial form of the wearable device based on the adjustment parameter that is detected;
    wherein the adjustment apparatus changes ventilation of the wearable device relative to a body part of the user.

10. The method according to claim 9, further comprising exchanging data between a mobile terminal and the wearable device.

11. The method according to claim 10, wherein the adjustment parameter is received from the mobile terminal by a communication unit of the wearable device.

12. The method according to claim 9, comprising retaining a body part of a user with part of the wearable device.

13. The method according to claim 12, wherein the part defines a cavity with an opening.

14. The method according to claim 13, comprising, after the body part of the user enters the cavity, sensing and retaining a relative position of the part and the body part of the user.

15. The method according to claim 14, comprising:
    detecting that the relative position has changed; and
    thereafter driving the adjustment apparatus to adjust the wearable device.

16. The method according to claim 9, wherein the adjusting comprises changing a relative tightness of the wearable device relative to a body part of the user.

17. A computer program product, comprising:
    a computer readable storage device comprising code, the code being executable by a processor of a wearable device and comprising:
    code that detects, at a wearable device, an adjustment parameter related to a spatial form adjustment for the wearable device, wherein the adjustment parameter is selected from the group consisting of an environmental parameter and a mode indication; and
    code that adjusts, using a control unit in communication with an adjustment apparatus of the wearable device and without user control input, the spatial form of the wearable device based on the adjustment parameter that is detected;
    wherein the adjustment apparatus changes ventilation of the wearable device relative to a body part of the user.

* * * * *